US012282901B2

United States Patent
Ha et al.

(10) Patent No.: US 12,282,901 B2
(45) Date of Patent: Apr. 22, 2025

(54) METHOD FOR PROVIDING FLEET SERVICE BASED ON SMELL INFORMATION AND APPARATUS FOR THE SAME

(71) Applicants: HYUNDAI MOTOR COMPANY, Seoul (KR); KIA CORPORATION, Seoul (KR)

(72) Inventors: Jae Jun Ha, Hwaseong-si (KR); Young Jun Moon, Sejong-si (KR); Tae Hee Lee, Yongin-si (KR)

(73) Assignees: HYUNDAI MOTOR COMPANY, Seoul (KR); KIA CORPORATION, Seoul (KR)

( * ) Notice: Subject to any disclaimer, the term of this patent is extended or adjusted under 35 U.S.C. 154(b) by 476 days.

(21) Appl. No.: 17/726,115

(22) Filed: Apr. 21, 2022

(65) Prior Publication Data

US 2022/0405716 A1 Dec. 22, 2022

(30) Foreign Application Priority Data

Jun. 21, 2021 (KR) ........................ 10-2021-0079777

(51) Int. Cl.
*G06Q 10/20* (2023.01)
*G01N 33/00* (2006.01)
*G07C 5/00* (2006.01)
*G07C 5/08* (2006.01)

(52) U.S. Cl.
CPC ......... *G06Q 10/20* (2013.01); *G01N 33/0004* (2013.01); *G07C 5/008* (2013.01); *G07C 5/0808* (2013.01)

(58) Field of Classification Search
CPC .... G06Q 10/20; G01N 33/0004; G07C 5/008; G07C 5/0808
See application file for complete search history.

(56) References Cited

U.S. PATENT DOCUMENTS

| 10,776,643 | B1 * | 9/2020 | Meister | G08B 3/10 |
| 11,745,605 | B1 * | 9/2023 | Li | B60L 53/14 |
| | | | | 701/22 |
| 11,828,210 | B2 * | 11/2023 | Varughese | F01N 11/00 |
| 2022/0055441 | A1 * | 2/2022 | Varughese | G06Q 30/0251 |

OTHER PUBLICATIONS

Npl: S. Garrigues, T. Talou, D. Nesa, A. Gaset, Modified GC/MS system versus dedicated MS device: comparative application of electronic nose for QC in automotive industry, Sensors and Actuators B: Chemical, vol. 78, Issues 1-3 (Year: 2001).*

* cited by examiner

*Primary Examiner* — Hitesh Patel
*Assistant Examiner* — Tabitha Kress
(74) *Attorney, Agent, or Firm* — MCDONNELL BOEHNEN HULBERT & BERGHOFF LLP

(57) ABSTRACT

A method for providing a fleet service based on smell information includes, while the moving object is being used in the fleet system, monitoring smell information of a moving object, controlling an operation of the moving object based on the smell information, and determining a return zone of the moving object based on the smell information.

17 Claims, 11 Drawing Sheets

METHOD FOR PROVIDING FLEET SERVICE BASED ON SMELL INFORMATION AND APPARATUS FOR THE SAME

CROSS REFERENCE TO RELATED APPLICATIONS

The present application claims priority to Korean patent application 10-2021-0079777, filed Jun. 21, 2021, the entire contents of which are incorporated herein for all purposes by this reference.

BACKGROUND

Field

The present disclosure relates to a method and apparatus for providing a fleet service. Particularly, the present disclosure relates to a method and apparatus for operating a fleet service by reflecting smell information which is generated in a moving object.

Description of the Related Art

Along with technical advances, the notion of car ownership is being weakened, while the use of shared cars is on the rise. Specifically, for the convenience of everyday life in a particular region or residence, the needs for shared vehicles and related services are increasing.

As a shared moving object service is managed by multiple users who are allocated shared moving objects at random and use the moving objects, the moving objects are not kept clean by users and consumables of moving objects are not properly managed.

As the cleanliness and smell of moving objects are important factors that users consider in evaluating the quality of a fleet service, an operator providing the fleet service should manage carefully the cleanliness and smell of moving objects.

According to the conventional method of managing moving objects, each operator providing a fleet service cleans periodically moving objects or exchanges consumables. However, such time-based periodic management of moving objects has limitations in keeping moving objects clean, which are exposed to various situations.

SUMMARY

In order to minimize discomfort related to poor cleanliness or smell, which is experienced by a user using a fleet service, it is necessary to monitor smell or cleanliness of a moving object and to clean the moving object or remove a cause of smell as immediately as necessary.

The present disclosure may provide a method and apparatus for monitoring the condition of a moving object and managing the moving object efficiently according to the monitored condition by using a fleet system that is implemented by a computing apparatus.

The technical objects of the present disclosure are not limited to the above-mentioned technical objects, and other technical objects that are not mentioned will be clearly understood by those skilled in the art through the following descriptions.

The present disclosure relates to a method, apparatus and system for allocating a moving object for a fleet system. The embodiments below may be commonly applied to a method, apparatus and system for allocating a moving object for a fleet system according to the present disclosure.

According to one aspect of the present disclosure, a method for providing a fleet service based on smell information includes monitoring smell information of a moving object, while a user is using the moving object in the fleet system, controlling an operation of the moving object based on the smell information, and determining a return zone of the moving object based on the smell information.

According to one aspect of the present disclosure, the monitoring of the smell information of the moving object may include checking at least one of a smell type and a smell strength.

According to one aspect of the present disclosure, the smell type may include at least one of a smell caused by an interior material or a consumable of the moving object and an abnormal smell.

According to one aspect of the present disclosure, the controlling of the operation of the moving object may include controlling to make outside air flow into the moving object in response to the smell strength that comes to exceed a predetermined threshold.

According to one aspect of the present disclosure, the controlling of the operation of the moving object may include providing at least one of the smell type and the smell strength through an entity capable of being recognized by the user.

According to one aspect of the present disclosure, the monitoring of the smell information of the moving object may include checking the smell strength according to the smell type.

According to one aspect of the present disclosure, the determining of the return zone of the moving object may include determining the return zone of the moving object as a cleaning zone, when the smell strength exceeds a predetermined first threshold.

According to one aspect of the present disclosure, the determining of the return zone of the moving object may include determining the return zone of the moving object as an emergency maintenance zone, when the smell strength exceeds a predetermined second threshold.

According to one aspect of the present disclosure, the smell strength may include a smell strength corresponding to each of the smell type.

According to one aspect of the present disclosure, the smell strength may be a strength for the abnormal smell.

According to one aspect of the present disclosure, the checking of at least one of the smell type and the smell strength may include checking a basic smell pattern based on data that are measured while the user does not use the moving object and the outside air is shut off for a predetermined time.

According to one aspect of the present disclosure, the checking of at least one of the smell type and the smell strength may include checking a current gas component distribution pattern based on data, which are measured while the user uses the moving object, and determining the smell type by using a result of comparison between the basic smell pattern and the current gas component distribution pattern.

According to one aspect of the present disclosure, the checking of at least one of the smell type and the smell strength may include checking environment information of the moving object, and determining the smell type by considering the environment information of the moving object and the current gas component distribution pattern.

According to one aspect of the present disclosure, the checking of at least one of the smell type and the smell strength may include checking activity information of the user, and determining the smell type by considering the activity information of the user and the current gas component distribution pattern.

According to one aspect of the present disclosure, the monitoring of the smell information of the moving object may include detecting smell information that is generated from at least one zone of the moving object, and monitoring the smell information of the moving object by using at least one piece of smell information corresponding to the at least one zone.

According to another aspect of the present disclosure, a moving object may be provided which is used in a fleet service. The moving object may include at least one transceiver, at least one smell sensor, a smell information monitoring unit, which is configured to monitor smell information based on data detected from the smell sensor, and at least one processor configured to control the at least one transceiver and the smell information monitoring unit.

The at least one processor may be further configured to control an operation of the moving object based on the smell information, to identify a return zone of the moving object based on the smell information and to provide the return zone of the moving object.

According to another aspect of the present disclosure, a server apparatus may be provided which manages a fleet service. The server apparatus may include at least one transceiver configured to transmit and receive a signal and at least one processor configured to control the at least one transceiver. Herein, the at least one processor may be further configured to provide the fleet service through at least one moving object or at least one user terminal, to identify smell information provided from the at least one moving object, to identify a return zone of the moving object based on the smell information and to manage the return zone of the moving object.

The features briefly summarized above with respect to the present disclosure are merely exemplary aspects of the detailed description below of the present disclosure, and do not limit the scope of the present disclosure.

The present disclosure may provide a method and apparatus for monitoring the condition of a moving object and managing the moving object efficiently according to the monitored condition by using a fleet system that is implemented by a computing apparatus.

The technical objects of the present disclosure are not limited to the above-mentioned technical objects, and other technical objects that are not mentioned will be clearly understood by those skilled in the art through the following descriptions.

DETAILED DESCRIPTION

Figure 1:
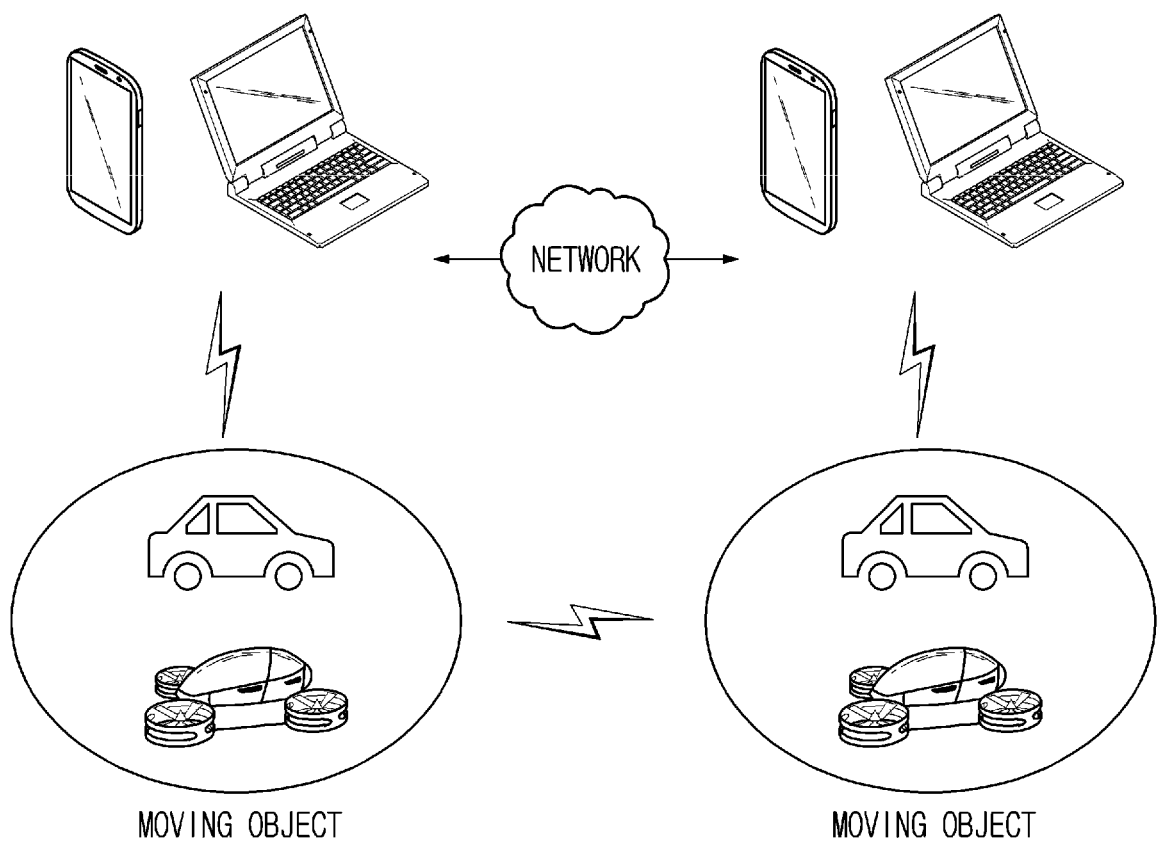
FIG. 1 is a view illustrating that a moving object communicates with another apparatus via a network.

Hereinafter, embodiments of the present disclosure will be described in detail with reference to the accompanying drawings, which will be easily implemented by those skilled in the art. However, the present disclosure may be embodied in many different forms and is not limited to the embodiments described herein.

In the following description of the embodiments of the present disclosure, a detailed description of known functions and configurations incorporated herein will be omitted when it may make the subject matter of the present disclosure rather unclear. Parts not related to the description of the present disclosure in the drawings are omitted, and like parts are denoted by similar reference numerals.

In the present disclosure, when a component is referred to as being "linked", "coupled", or "connected" to another component, it is understood that not only a direct connection relationship but also an indirect connection relationship through an intermediate component may also be included. Also, when a component is referred to as "comprising" or "having" another component, it may mean further inclusion of another component not the exclusion thereof, unless explicitly described to the contrary.

In the present disclosure, the terms first, second, etc. are used only for the purpose of distinguishing one component from another, and do not limit the order or importance of components, etc. unless specifically stated otherwise. Thus, within the scope of this disclosure, a first component in one exemplary embodiment may be referred to as a second component in another embodiment, and similarly a second component in one exemplary embodiment may be referred to as a first component.

In the present disclosure, components that are distinguished from each other are intended to clearly illustrate each feature. However, it does not necessarily mean that the components are separate. That is, a plurality of components may be integrated into one hardware or software unit, or a single component may be distributed into a plurality of hardware or software units. Thus, unless otherwise noted, such integrated or distributed embodiments are also included within the scope of the present disclosure.

In the present disclosure, components described in the various exemplary embodiments are not necessarily essential components, and some may be optional components. Accordingly, exemplary embodiments consisting of a subset of the components described in one embodiment are also included within the scope of the present disclosure. Also, exemplary embodiments that include other components in addition to the components described in the various embodiments are also included in the scope of the present disclosure.

Advantages and features of the present disclosure, and methods for achieving them will be apparent with reference to the exemplary embodiments described below in detail with reference to the accompanying drawings. However, the present disclosure is not limited to the exemplary embodiments set forth herein but may be embodied in many different forms. The present exemplary embodiments are provided to make disclosed contents of the present disclosure thorough and complete and to completely convey the scope of the disclosure to those with ordinary skill in the art.

Although exemplary embodiment is described as using a plurality of units to perform the exemplary process, it is understood that the exemplary processes may also be performed by one or plurality of modules. Additionally, it is understood that the term controller/control unit refers to a hardware device that includes a memory and a processor and is specifically programmed to execute the processes described herein. The memory is configured to store the modules and the processor is specifically configured to execute said modules to perform one or more processes which are described further below.

FIG. 1 is a view illustrating that a moving object communicates with another apparatus via a network.

Referring to FIG. 1, a moving object may communicate with another moving object or another device. Herein, as an example, the moving object may communicate with another moving object or another device based on cellular communication, WAVE communication, dedicated short range communication (DSRC), or other communication schemes. That is, as a cellular communication network, a communication network such as LTE, 5G, WiFi communication network, WAVE communication network, etc. may be used. In addition, a local area network used in a moving object, such as DSRC may be used, and the present disclosure is not limited to the above-described embodiment.

In addition, as an example, for the purpose of security of a moving object with respect to communication of the moving object, a module capable of communicating only with a device inside the moving object and a module capable of communicating with a device outside the moving object may exist separately. As an example, inside the moving object, communication based on the security such as Wi-Fi communication may be performed only for a device within a certain range in the moving object. As an example, the moving object and a personal device owned by the moving object driver may include a communication module for performing communication only with each other. That is, the moving object and the personal device of the moving object driver may use a communication network disconnected from an external communication network. Also, as an example, the moving object may include a communication module for performing communication with an external device. In addition, as an example, the above-described module may be implemented as a single module. In other words, based on a single module, a moving object may communicate with anther device, which is not limited to the above-described embodiment. That is, in a moving object, communication may be performed based on various methods and is not limited to the above-described embodiment.

Herein, for example, a moving object may refer to a device capable of moving. As an example, a moving object may be a vehicle (including an autonomous vehicle or an automated vehicle), a drone, a personal mobility device, a mobile office, a mobile hotel or a personal air vehicle (PAV). "Personal mobility device" may include for example a moving object including at least three wheels for stable independent driving or a moving object (e.g., a single-wheeled segway, a two-wheeled segway, an electric scooter, etc.) that has one or two wheels but is capable of being driven independently by keeping its balance. A personal mobility device may use electricity as a power source by means of a battery but is not limited thereto and may utilize any type of power sources capable of moving the mobility. As an example, a personal mobility device may mean a means of transportation that may be taken or used by only one user. In addition, a personal mobility device may mean a means of transportation that a small number of users may use as a small means of transportation. As an example, not only a single-wheeled segway, a two-wheeled segway and an electric scooter but also an electric wheelchair, an electric bicycle and an electric two-wheeled vehicle may be a personal mobility device. In addition, a moving object may be any other moving apparatus and is not limited to the above-described embodiment.

Figure 2:
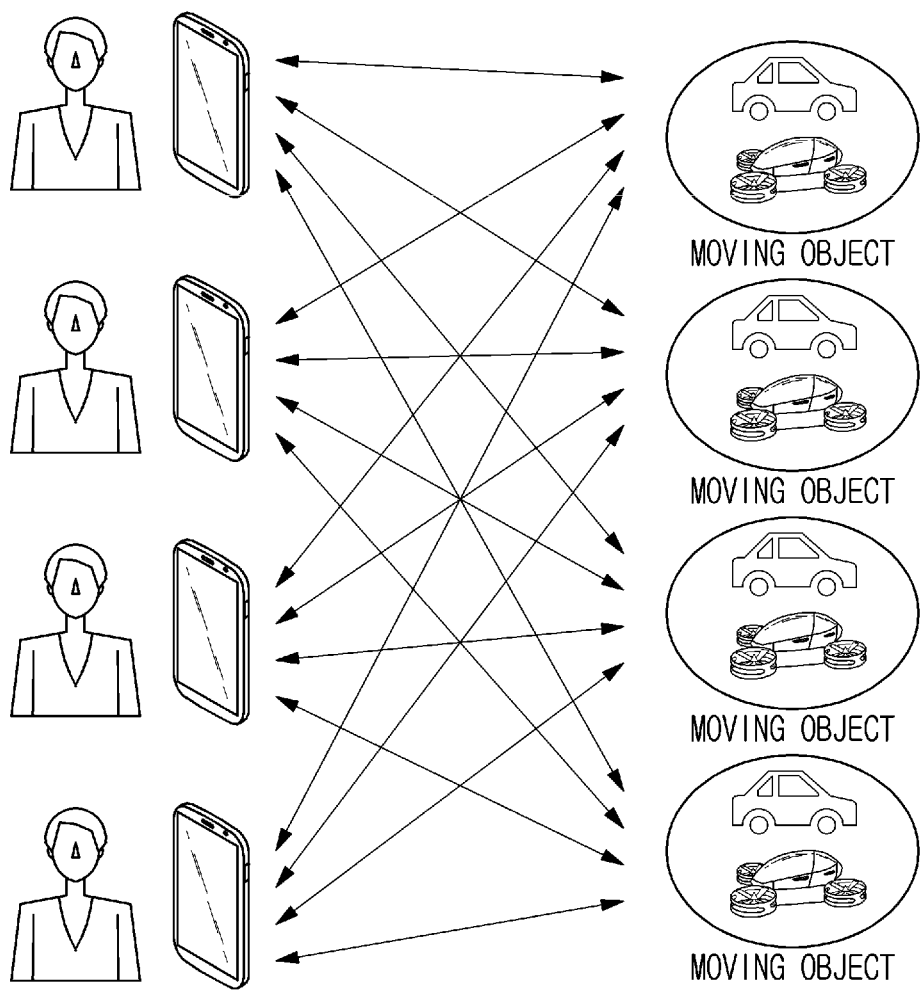
FIG. 2 is a view illustrating that a moving object is shared based on a fleet system.

FIG. 2 is a view illustrating that a moving object is shared based on a fleet system.

As an example, a fleet system may be applied to provide a moving object sharing service. Herein, the fleet system may be operated by data generation, processing and exchange between computing apparatuses. For example, a fleet system may be a system including at least one server, a multiplicity of user devices and a multiplicity of moving objects. For a fleet service, a server may process a request of a user device, transmit a response message, and manage a moving object by processing the reservation and allocation/return of the moving object according to the request. Furthermore, the server may generate status information of every moving object by receiving moving object state information from moving objects so that overall information associated with moving objects may be managed. The server may implement a disposition process of a moving object, of which the sell-by-date disposal is near or at hand, through mutual data exchange between a related user device and the moving object by using an application or program embedded in the server.

In addition, a fleet system may be a system including a multiplicity of devices and a multiplicity of moving objects. In addition, as an example, the fleet system may further include a road side unit (RSU) and the like. Herein, a device may be a smart phone, a smart pad and a smart watch. As another example, a device may be an apparatus capable of performing other communication and exchanging a signal, which is not limited to the above-described embodiment. However, for the convenience of explanation, the terms "device" or "user device" will be used in the description below. In addition, as an example, a moving object may be a vehicle. In addition, as an example, a moving object may be an object moving on rails or other constructed areas. As another example, a moving object may be a flying object like drone. That is, a moving object may refer to an object capable of moving and mean a shared moving object based on a fleet system. For the convenience of explanation, a moving object will refer to a vehicle in the description below. This may be applied to other moving objects in the same way. As another example, a RSU may be a roadside apparatus capable of communication. In addition, as an example, a RSU may refer to a structure installed for transmitting and receiving a signal to and from a building or another area, which is not limited to the above-described embodiment. However, for convenience of explanation, such structures will be referred to as RSUs in the description below. RSUs may be various structures or apparatus, which is not limited to the above-described embodiment.

In addition, a fleet system may be a moving object sharing system. A fleet system may be a system in which a moving object is shared in a certain area. Herein, the certain area may be a local concept, such as an apartment complex, a work place, and the like. As an example, the certain area may include an area in an apartment complex or an area a predetermined distance around the apartment complex. As another example, the certain area may mean an area a predetermined distance around the work place. As another example, an area to which a fleet system is applied may be a larger area like an administrative district or a city, which is not limited to the above-described embodiment. That is, the certain area may mean a reference range capable of operation based on a fleet system, and may be changed by a user or a system.

In addition, as an example, a fleet system may be a system in which a moving object is shared with a user authenticated as a specific user (or device). As an example, a specific user may be a resident of an apartment in a predetermined range of area or a worker of an office located in a particular region, in which a service of a fleet system may be provided. As an example, the specific user may be a subscriber to a fleet system available in a predetermined service area and be a user outside the service area. Such a user may be a person who wants to use a sharing service when approaching a predetermined service area. As an example, a fleet system may provide a moving object sharing service based on a device that an apartment inhabitant and/or an office worker has registered. Thus, a sharing service may be provided only to a specific person, and the safety and management efficiency of a moving object may be enhanced. However, a specific user using a shared moving object in a fleet system may be determined based on another method, which is not limited to the above-described embodiment.

In a shared moving object fleet system, a shared moving object may be provided. Here, a shared moving object may be a moving object that has been authenticated and approved to be shared by a system. As an example, the shared moving object may be a moving object registered in the fleet system. Here, a fleet system manager may provide a shared moving object for the fleet system. That is, only a moving object authenticated or authorized by the fleet system manager may be used as a shared moving object. Thus, an accident that could occur due to the safety or management of a moving object in a fleet system may be prevented beforehand. Specifically, a moving object to be shared may be registered in a fleet system. A right to register a moving object as a shared moving object in a fleet system may be restricted by the fleet system. Herein, a moving object capable of being registered in the fleet system may have a same ID or same identification information. In addition, as a fleet system provides a shared moving object, the management for the shared moving object may be performed. As an example, the management of a shared moving object may be necessary to provide a shared moving object service, such as residual oil information, moving object state information, or moving object driving information for the moving object registered in a fleet system. Herein, the fleet system may check the state of a shared moving object in real time, and for a moving object having a problem, the permission for use may be restricted or a command of repair may be delivered through the system, based on which a service may be provided.

As another example, a fleet system may provide a mixture of a shared moving object and a privately-owned moving object. As an example, the fleet system may set identification information, such as a moving object type indication field, to distinguish a shared moving object provided by the system and a privately-owned moving object. Herein, when the indication field is recorded as a value of not privately-owned moving object, it may indicate a shared moving object that is not privately owned but is provided by a system provider. On the other hand, when the indication field is recorded as a value indicating a privately-owned moving object, it may indicate there is a moving object privately owned and the moving object is provided as a shared moving object in a fleet system. It is also possible to consider a case in which a privately-owned moving object and a shared moving object provided by a system are mixed. Herein, as an example, the fleet system may provide different services based on a moving object type indication field. As an example, in the case of a moving object provided by the fleet system, there may be no restriction of use for a user who uses the moving object. On the other hand, in the case of a privately-owned moving object, there may be a restriction of use. As another example, in a fleet system moving object and a privately-owned moving object, a service may be provided based on different charging systems, which is not limited the above-described embodiment.

As another example, in relation to a specific operation of a fleet system, a service may be provided based on a device registered to the fleet system.

Specifically, the device registered to the fleet system may obtain information on a shared moving object after authentication and security procedures with the system. That is, from the perspective of the device, information on the shared moving object may be provided. Herein, the device may contact the moving object to be used based on the information on the shared moving object.

As an example, there may be a moving object and a device (or users) that are registered to a fleet system. That is, based on authentication and authorization, only specific moving objects and devices may be registered to the fleet system. Herein, the fleet system may be operated based on state information of the registered moving objects and the registered devices. As an example, the fleet system may check information on a moving object currently in use and location information on an individual moving object in real time. Herein, as an example, each moving object may periodically transmit its information to the fleet system. In addition, as an example, each moving object may transmit its information to the fleet system based on an event trigger. As an example, when an event of a change in location or in whether or not to use is triggered to a moving object, the moving object may transmit its information to the fleet system (or server).

In addition, the fleet system (or server) may check information on a registered device in real time. Herein, as an example, the registered device may not always use a service of the fleet system. Accordingly, activation information indicating whether a registered device uses a service of a fleet system may be needed. Herein, as an example, the fleet system may include list information for a registered device. Among registered devices included in a list of a fleet system, a device, which is currently using a moving object or activates the system to use the moving object may be provided along with list information. As another example, devices may be indicated by being classified into registered devices (deactivated devices) that do not use a fleet system, registered devices (activated devices) that are using a moving object of the fleet system, and registered devices (temporary devices) that are willing to use a moving object. That is, information may be provided whether a device is actually using a micro mobility, does not want to use any micro mobility or wants to use a micro mobility but not uses one yet. In addition, as an example, for a device using a moving object of a fleet system, usage state information may further be indicated. As an example, usage state information may further include information on expected time of use or information on location of use.

Specifically, a fleet system may include list information on a multiplicity of moving objects and a multiplicity of devices that are registered. Herein, the list information may include at least one or more among usage state information, device location information, and moving object location information. Herein, the fleet system may provide a moving object sharing service based on the device location information and the moving object location information. In addition, the above-described usage state information may include at least one or more among information on a moving object in use, information on expected time of the moving object in use, device-moving object matching information, deactivated device information, activated device information, deactivated moving object information, and activated moving object information. Herein, as an example, the usage state information may further include information on a moving object in use that is being used by another device and information on expected time of the moving object in use.

In addition, the usage state information may further include device-moving object matching information based on information in a list form. In addition, the usage state information may include activated device information and deactivated device information. As an example, as described above, the activated device information may be a device that is preparing to use a current moving object among devices registered to a fleet system. As an example, the activated device may mean a device that executes a program or an application for the fleet system. Meanwhile, the deactivated device may be a device that is registered to the fleet system but does not use moving object sharing. As an example, the deactivated device may be a device that does not execute or deactivates a program or application for the fleet system.

In addition, a fleet system may include activated moving object information and deactivated moving object information. In this case, as an example, the fleet system may include state information on a multiplicity of moving objects. Herein, the state information on a moving object may be information on the moving object, such as information on whether or not there is abnormality of the moving object, information on remaining distance to drive, or information on energy source replenishment time. In other words, state information on a moving object may be information for determining whether or not the moving object may be provided for sharing, which is not limited to the above-described embodiment. Herein, the fleet system may determine whether or not to activate the moving object based on the above-described state information. As an example, for a moving object that has no abnormality of state and has a sufficient residual amount of energy, a fleet system may provide information on the moving object as an activated moving object.

A residual amount of energy may be differently understood according to a type of energy source of a moving object. When a moving object has an internal-combustion engine employing gasoline, diesel, natural gas or LPG as a main energy source, the residual amount of energy may be a refuel volume or charged volume. When a moving object is an electric energy-based apparatus that generates a driving force by means of a motor employing electricity as main energy source, the residual amount of energy may be residual electric power. When a moving object is a hybrid engine equipped both with an internal-combustion engine and an electric motor, the residual amount of energy may be a refuel volume. When a moving object includes a hydrogen energy-based apparatus that generates electricity in a fuel cell by employing hydrogen as main energy source and generates a driving force of a motor using the generated electricity, the residual amount of energy may be a residual amount of gaseous hydrogen or liquid hydrogen in a tank. When a moving object includes a solar energy-based apparatus that employs sunlight, which is collected through a photovoltaic panel, as main energy source, provides and accumulates power in a battery, and generates a driving force of motor using supplied power, the residual amount of energy may be a residual amount of electric power accumulated in the battery. A solar energy-based moving object may not be provided as an activated moving object according to an expected use distance desired by a user and weather conditions, even when there is a residual amount of electric power. Vehicles like sedans and SUVs, high occupancy vehicles, vehicles for carrying loads, two-wheeled motorcycles, and personal mobility devices may be equipped with any one of the above-described engines or apparatuses.

On the other hand, the fleet system may classify a moving object with abnormality as a deactivated moving object. Herein, the fleet system may provide information on the deactivated moving object to an associated system or server. As an example, the associated system or server may perform repair or management for a deactivated moving object, which is not limited to the above-described embodiment.

In addition, as an example, a fleet system may classify a moving object with a residual amount of energy below a predetermined level as a deactivated moving object, as described above. As another example, when a moving object with a residual amount of energy below a predetermined level is shared through a device, a fleet system may provide a device user with information on the residual amount of energy through notification. In addition, as an example, a fleet system may provide a user with information on an associated designated system (e.g., an energy replenishment facility of a particular brand, an electric vehicle charging station, a liquid or gas hydrogen charging station and the like) and also information reminding that an energy source needs to be replenished. Herein, the fleet system may exchange charging information or other necessary information with a designated associated system regardless of the user, thereby providing a service.

That is, a user using a moving object sharing system may replenish an energy source at a designated place without paying a fee, and the fee may be processed through the fleet system and an associated system. Meanwhile, as an example, as described above, a device (temporary device) willing to use a moving object may want to use the moving object by checking a fleet system.

As an example, a moving object to be used may be allocated to a device through a fleet system. Herein, as an example, the fleet system or server may allocate the moving object to the device by using at least one of information on the moving object in use, location information of the moving object, and location information of the device. Meanwhile, as an example, when the fleet system cannot allocate any moving object, the fleet system may provide the device with information on the failure. In addition, as an example, the fleet system may allocate only a moving object within a predetermined distance from the location of the device, which is not limited to the above-described embodiment. Next, the device may come within the predetermined distance from the moving object. Here, the device may transmit an authentication signal to the moving object. In addition, as an example, the device may use a shared moving object by tagging the shared moving object based on a list of available moving objects. As an example, the device may tag a moving object based on NFC, Bluetooth, or a magnetic means like a transportation card. Herein, when the device tags a shared moving object, an authentication procedure from the fleet system may be performed to provide the moving object to the device. As an example, when the authentication is completed based on the device tagging, the door of the moving object may be opened.

As for a detailed operation for authentication, when a device approaches a moving object within a predetermined distance, an authentication signal may be transmitted to the moving object. Herein, communication available to the moving object and the device may be Bluetooth, NFC or tag, as described above. That is, a procedure for authentication may be performed under certain conditions, which is not limited to the above-described embodiment. When the device approaches or tags the moving object, the moving object and the device may exchange a signal so that whether or not the device may use the moving object is determined and the device is authenticated. Herein, the device may transmit, to the moving object, an authentication signal including its identification information and identification information of a group in which the device is included. Here, based on the identification information of the device included in the authentication signal thus received, the moving object may verify whether or not the device is registered to a fleet system. In addition, based on the identification information of a group included in an authentication signal, a moving object may confirm whether or not the device is included in a group to which the moving object may provide a service. In other words, based on device identification information and group identification information, a moving object may determine whether or not a device may use the moving object. As an example, when the device is incapable of using the moving object, the moving object may transmit information on unavailability to the device. As an example, the device may obtain the information on unavailability from an application or another service providing program.

Meanwhile, when the device is capable of using the moving object, the moving object may transmit a signal requesting the execution of an authentication procedure to the device. That is, when the device is legally registered to the above-described fleet system (or server) and the moving object is capable of operating legally based on the fleet system, the moving object may transmit the signal requesting the execution of the authentication procedure to the device. Herein, the moving object may include its own identification information and encryption key information in a signal for requesting the execution of an authentication procedure and transmit the signal to the device. As an example, both the moving object identification information and the device information may be registered to the fleet system. In this case, the moving object may transmit a signal including the moving object identification information, the device identification information, and the encryption key information to the fleet system.

In addition, the device may also transmit a signal including identification information of a moving object, encryption key information and its own identification information, which are included in a signal requesting the execution of an authentication procedure, to the fleet system.

Then, the fleet system may compare information included in the signal received from the moving object and information included in the signal received from the device. Herein, when the moving object identification information, the device identification information, and the encryption key information all agree, the fleet system may recognize that the device is capable of using the moving object. Then, the fleet system may transmit authentication confirmation information to the moving object and the device. Herein, the fleet system may register, to a database, information indicating that the device uses the moving object. In addition, as an example, time for the device to use the moving object and additional information may be continuously transmitted.

In addition, the moving object may register the device based on the authentication confirmation information and may open the door of the moving object. In addition, a lock may be released to use the moving object, whereby the device may control the moving object.

Herein, as an example, when the above-described authentication is completed, the moving object and the device may periodically exchange signals. That is, while the device uses the moving object, the moving object may continuously confirm the use by periodically exchanging signals with the device.

Figure 3:
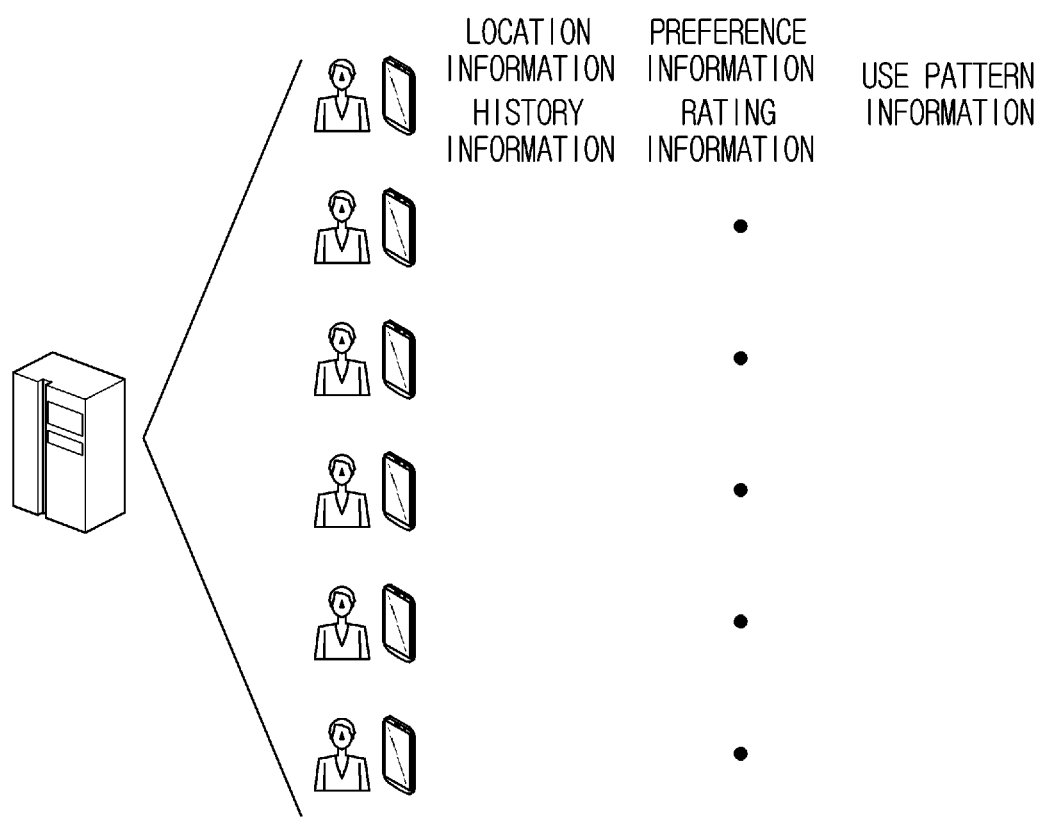
FIG. 3 is a view illustrating that a user is managed based on a fleet system.

FIG. 3 is a view illustrating that a user is managed based on a fleet system.

As an example, based on the above-description, a moving object and a device may be managed in a fleet system. Herein, as an example, information of each user may be managed in the fleet system. As an example, information of each user may be information on the user' use based on user identification ID or the user's identification device. As a more concrete example, information of each user may include at least one or more among information on the user's location, information on the user's history, information on the user's preference, information on use status, rating information, and use pattern information. As an example, information on the user's location may be information for identifying the user's main route while using a fleet system. As an example, a user's location information may be static location information set by the user like the user's residence and place of work and dynamic location information like location information at time of use request and location information at expected time of use. In addition, as an example, a fleet system may store history information of a user. History information may be information on a user's propensity, which is analyzed based on a type of a moving object used by a user, a zone used in a fleet spot provided to a fleet system, a travel route, a destination point, and a parking point during use. As an example, a fleet system may perform recommendation for the use of a moving object based on a user's history information. In addition, as an example, a fleet system may perform management for allocating and distributing a moving object by using history information of a multiplicity of users. In addition, as an example, a fleet system may include information on a user's preference. As an example, information on a user's preference may be information considering the frequency or preference of a moving object in use. Specifically, preference information may be a type of the moving object that is designated or estimated by the user as a preferred moving object. In addition, as an example, a user's preference information may be information input by the user, which is not limited to the above-described embodiment.

In addition, as an example, a fleet system may provide rating information of a user. Rating information may be rating levels given to each user based on use state information including subscription information for a fleet system and use performance information and after-use evaluation information. As an example, subscription information may be information on whether or not a long-term contract is made as a contract condition for a service of a fleet system and whether or not premium membership is signed up. Use performance information may include a frequency with which a user uses a moving object, a fee according to time or distance, and the like. As an example, when a user frequently uses a moving object, the rating may be raised. In addition, in relation to evaluation information, a rating level may be lowered when a user smokes or causes bad smell in a moving object and a subsequent user or a manager makes a comment of poor use or such a comment is accumulated. In addition, in relation to evaluation information, a rating level may be raised when a moving object is used without an accident or in a continuously good condition so that no unnecessary maintenance work is needed.

Figure 4:
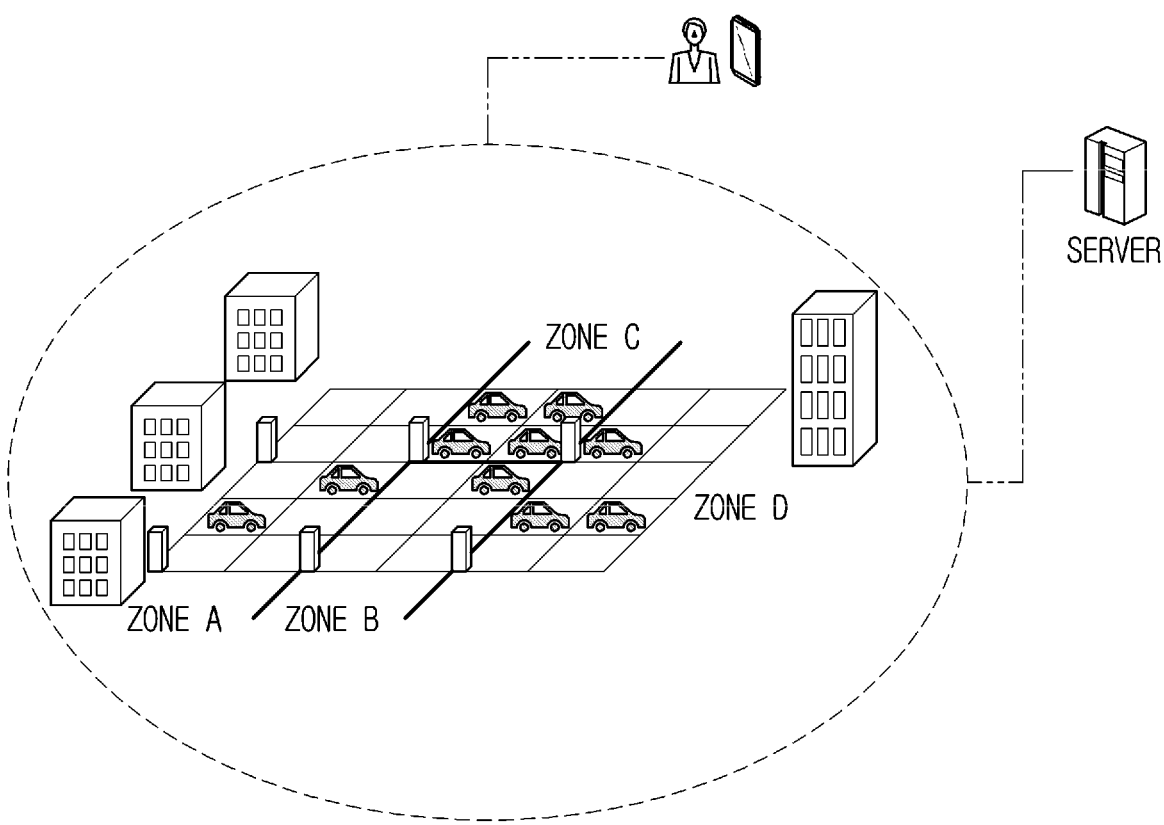
FIG. 4 is a view illustrating an example of a fleet spot according to an embodiment of the present disclosure.

FIG. 4 is a view illustrating an example of a fleet spot according to an embodiment of the present disclosure.

A fleet system may have and operate a fleet spot that is a space in which a shared moving object may be allocated and returned. A fleet spot may be a region in which a shared moving object is kept and a service is provided in a predetermined area. As an example, the predetermined area may be located as an area near a region dense with residential districts and/or commercial districts. This aims to enable a fleet system to enhance the convenience of a service for persons using buildings near residential and/or commercial buildings holding many people or a large floating population. People who are likely to use a fleet system include not only inhabitants of buildings but also other people using the fleet system for various purposes like visiting a neighboring area of a fleet spot or transferring to another moving object via the fleet spot.

A fleet system according to the present embodiment may be operated by a small number of moving objects and be operated also by a large number of moving objects for expanding services and ensuring convenience through the fleet system. When being operated by a large number of moving objects, a fleet spot may have a large area of space for holding various types of many moving objects. When a fleet spot is operated in a large area of space, a lot of moving objects may be deployed to be held uniformly across the large space and be deployed by considering a building around the fleet spot, the number of residents, a floating population, and the like. Accordingly, a fleet spot may be divided into a multiplicity of zones, as shown in FIG. 4, in order to efficiently manage many moving objects. A holding area and a parking space may be allocated to a zone by considering information of the neighboring area of the zone such as a building around a fleet spot, the number of residents, a floating population, and the like. For example, in the case of Zone A near an area dense with commercial buildings, by considering the number of residents of a building, the number of visitors, an expected purpose of a moving object (e.g., outside duty, delivery, non-occupational personal business, etc.) and average use state of a moving object (e.g., cleanliness, frequency of request of light maintenance, long travel, average number of passengers, etc.), small-sized sedans, medium-sized sedans, 7-to-11 seater vehicles and personal mobility devices may account for a large percentage of moving objects, while large-sized premium sedans may be allocated at a low percentage. In addition, among small and medium-sized vehicles allocated to Zone A, a larger number of vehicles may have intermediate and excellent levels in detailed aspects like age and cleanliness rather than top level, and as for large-sized premium vehicles, excellent and top levels may account for a larger percentage.

As another example, in the case of Zone D near a residential region, moving objects are used mainly for personal purposes like shopping, commuting, riding with family, and many other purposes belonging to personal life styles, and clean use and frequency of requesting light maintenance may be relatively better. Based on this, small to large-sized sedans and 7-to-11 seater vehicles may be uniformly allocated in Zone D, and vehicles with excellent to top levels in age and cleanliness may be allocated to account for a relatively large percentage.

As another example, a fleet system may induce a user of a moving object to return the moving object not to an original return zone but to a maintenance zone, when the fleet system determines the need of urgent maintenance based on the state information of the moving object.

As yet another example, a fleet system may induce a user of a moving object to return the moving object not to an original return zone but to a cleaning zone or a maintenance zone, when the fleet system determines the need of cleaning based on the state information of the moving object.

Hereinafter will be described that a fleet system implemented by a computing apparatus allocates a moving object.

A fleet system has an embedded application or program for allocating a moving object. For the convenience of explanation, such applications and programs will be collectively referred to as applications. An application may implement a moving object allocation process based on requests and data mutually transmitted among a user device, a shared moving object and a server. Such an application may be embedded in a user device, a shared moving object and a server so that the server may implement the process by obtaining information generated from each computing apparatus. For the convenience of explanation, it is mainly described that a server executes the process. However, for example, in order to secure a storage space of a server memory, data generated by using a moving object may be accumulated in a user device and/or the moving object, and the data thus accumulated until the time of request may be transmitted to the server at the request of the server.

Figure 5:
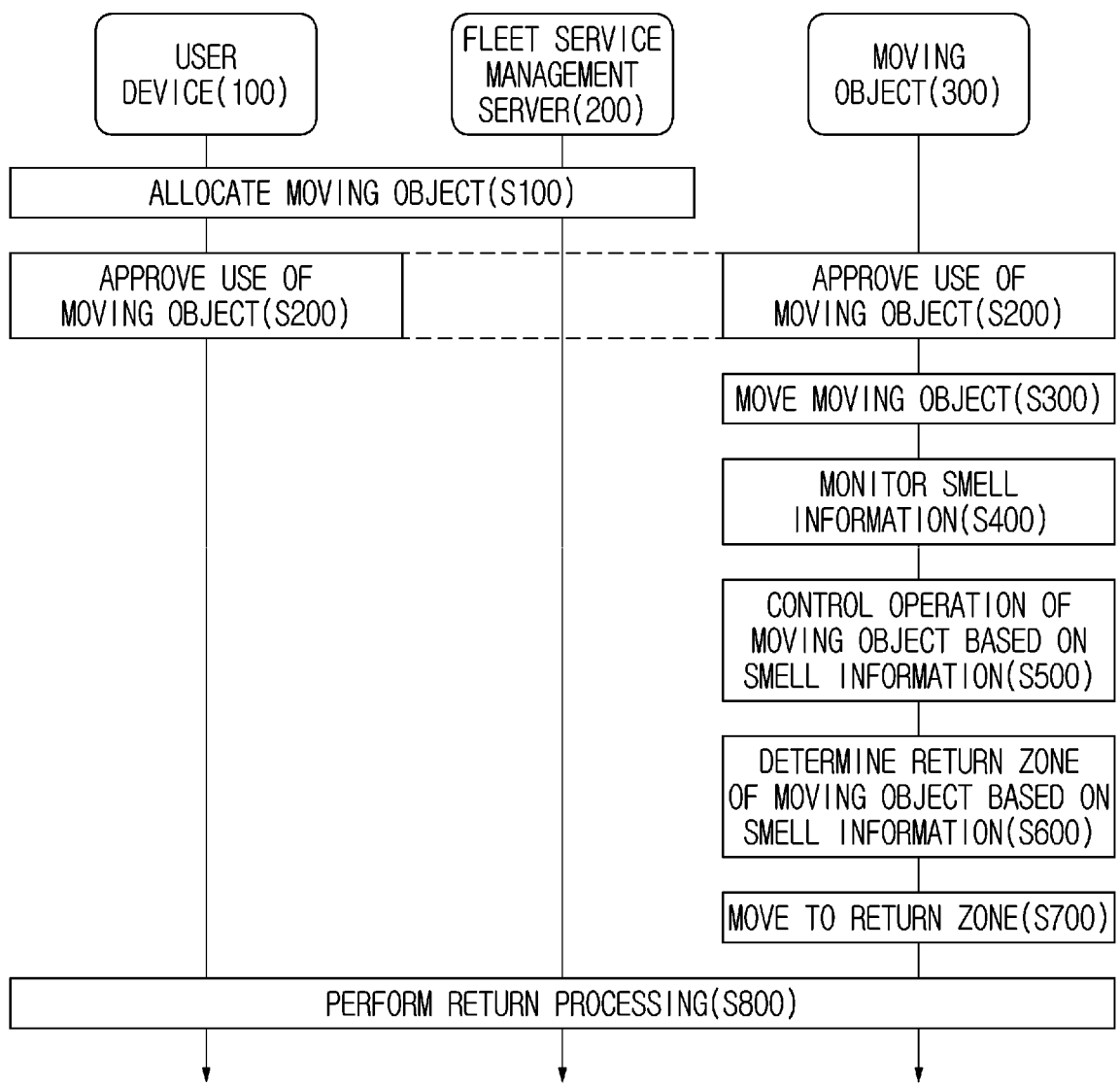
FIG. 5 is a flowchart illustrating an order in a method for providing a fleet service based on smell information according to an embodiment of the present disclosure.

FIG. 5 is a flowchart illustrating an order in a method for providing a fleet service based on smell information according to an embodiment of the present disclosure.

First, the method for providing a fleet service based on smell information according to an embodiment of the present disclosure may be implemented by a fleet system that includes a user device 100, a fleet service management server 200 and a moving object 300. Hereinafter, in the method for providing a fleet service based on smell information according to an embodiment of the present disclosure, the user device 100 will be 11-seater referred to as the device 100, and the fleet service management server 200 will be referred to as the server 200.

Referring to FIG. 5, the device 100 and the server 200 may perform an operation of allocating a moving object that a user will use at S100. The operation of allocating the moving object may be performed at a moving object use request of the device 100. As an example, the device 100 may make a use request for a moving object to the server 200. A use request may be a message that is generated by including time to use a moving object. As an example, a use request message may be generated by further including a user's location information together with time to use a moving object. As an example, a user's location information may be a residence or a place of work, which the user has registered. In addition, a user's location information may be location information at the time of making a use request, as confirmed by a device, or location information input as a location in which the user is expected to be present when using the moving object 300. For example, when a residence or a place of work is set as location information either basically or later, the location information may be determined. As another example, when location information at the time of use request other than a residence or a work of place is selected and is input, the location information may be set as a selected location.

Next, the server 200 may determine at least one zone meeting a use request and may check an available moving object list including an available moving object of the zone. When a use request is a message that is generated by time to use a moving object and a user's location information, the server may check a moving object available at the time of use in each zone by referring to scheduling of use of moving objects and may sort moving objects sequentially from a nearest zone to gradually further zones according to the user's location information among zones in which available moving objects are confirmed.

Although, in an embodiment of the present disclosure, a use request is exemplified to include time to use a moving object and a user's location information, the present disclosure is not limited thereto, and a use request may be configured to include various pieces of information. Also, the server 200 may configure an available moving object list by identifying available moving objects based on information included in a use request.

As another example, a use request may include rating information. A use request may be a message that is generated as a combination of a user's location information and rating information or rating information without location information, together with time to use a moving object. The server 200 may check a benefit and a penalty, which are given to a user making a use request according to a rating level of rating information, and determine a condition for allocating a moving object based on the checked benefit and penalty. For example, the server 200 may manage rating information based on cleanliness of a moving object which is used by a user. As an example, the server 200 may check cleanliness after a user uses a moving object and may calculate and store a cleanliness rating of the user by using the checked cleanliness. Cleanliness may be input by a manager or a next user or be checked through an instrument (e.g., camera, smell detection sensor) installed in the moving object.

Next, the server 200 may receive reservation information based on a moving object that the device 100 selects in an available moving object list.

As described above, in the case of a use request composed only of time of use, an available moving object list may be presented as a list of moving objects in an adequate zone according to use scheduling of a moving object.

Reservation information may include an identification number (e.g., license plate number) of a moving object selected from a list, time of use, and a parking space, which the device 100 select from a list.

Next, the server 200 may allocate a moving object to the device 100 based on reservation information.

When a user uses an actual moving object, the user may move to a parking space of a zone, which is set in reservation information, and may receive a moving object. As another example, when a user enters a zone of a fleet spot far from a parking space for a personal reason, the server 200 may move a moving object with autonomous driving function to the user's waiting location according to an adjacent delivery request of the device 100. The waiting location may be identified based on location information of the device 100. When a moving object has no function of autonomous driving, the server 200 may move the user to a parking space using a separate transportation means (e.g., unmanned shuttle operating in a fleet spot) according to an adjacent delivery request. Although, in an embodiment of the present disclosure, a user is exemplified to move to a moving object without autonomous driving function through a means of transportation, the present disclosure is not limited thereto, and various methods may be used in which the user is capable of using a moving object without autonomous driving function, while moving the user or the moving object. For example, it is possible to use, through an operation server, a method of moving a moving object without autonomous driving function to a user's location or various methods of moving the user to the moving object without autonomous driving function. A method of moving by a person or a service provider may be used as a method of moving a moving object without autonomous driving function to a location in which a user is present.

Next, the user may approach the moving object 300, while carrying the device 100, and may get approval of using the moving object 300 that is allocated through control of the server 200 which is connected with the device 100 and the moving object 300 at S200. As an example, the server 200 may provide approval information to the moving object 300, which is allocated to the user, and provide approval information to the device 100 of the user at the same time. In addition, as the user's device 100 approaches the moving object 300, the device 100 and the moving object 300 may process the use of the moving object 300 by exchanging the approval information that is provided by the server 200. Although, in an embodiment of the present disclosure, the approval of using the moving object 300 is exemplified to be processed through exchange of approval information between the device 100 and the moving object 300, the present disclosure is not limited thereto, and various modifications is possible.

As the approval of using the moving object 300 is completed, the user may get on the moving object 300, and the moving object 300 on which the user gets may be moved through the user's control or autonomous driving control at S300.

While the moving object 300 is being moved, the moving object 300 may monitor smell information of the moving object 300 through a smell detection sensor that is provided inside or outside at S400.

In particular, the moving object 300 may control driving of the moving object 300 based on the monitored smell information at S500. As an example, the moving object 300 may identify a smell type by analyzing components causing smell and may control a ventilator of the moving object 300 according to the identified smell type. As an example, the moving object 300 may identify a smell type and provide the smell type to the user through a display or an audio guide system installed in the moving object 300. As another example, the moving object 300 may provide the smell type to the user through the device 100.

Furthermore, the moving object may determine a return zone of the moving object 300 based on the monitored smell information at S600. As an example, the moving object may check information associated with smell-causing component analysis, identification of small type, inference of smell-causing factor, strength of smell, necessity of replacing parts, necessity of urgent cleaning and the like and may determine a return zone as a general parking zone, a maintenance zone or a cleaning zone based on the information thus checked.

Furthermore, a detailed operation for determining, by the moving object 300, a return zone will be described with reference to FIGS. 6 to 9 below.

Meanwhile, when a return zone of the moving object 300 is determined, the moving object 300 may be moved to the determined return zone at S700 and may perform return processing through the device 100 and the server 200 at S800. Herein, the server 200 may calculate and store a cleanliness rating for the user by using the smell information, which is monitored in the moving object 300, the return zone and the like. Additionally, the server 200 may calculate the cleanliness rating for the user by analyzing image information that is identified through a camera installed in the moving object 300.

Meanwhile, the moving object 300 may be equipped with a smell analyzer that detects smell information, and the smell analyzer may be equipped with at least one smell sensor that detects the physical properties (mass, absorbency, etc.) and chemical properties (absorption ratio, reaction, etc.) of a gas component. As an example, the smell sensor may include at least one of a metal oxide sensor, a polymer sensor, a photo-acoustic sensor, a surface plasmon resonance sensor, and a micro cantilever sensor.

Also, the smell analyzer may identify at least one gas component based on data, which are detected from at least one smell sensor, and identify a value for the gas component. Also, the smell analyzer may identify a smell type based on at least one gas component and a corresponding value. As an example, the smell analyzer may identify a smell type on its own. As another example, the smell analyzer may provide at least one gas component and a corresponding value to the fleet service management server 200 and may also receive a smell type that is analyzed by the fleet service management server 200.

Also, the smell analyzer may identify smell strength based on at least one gas component and a corresponding value. Likewise, the smell analyzer may identify smell strength by means of its own algorithm or by using the fleet service management server 200.

Based on what is described above, the smell analyzer may identify smell information including at least one of smell type and smell strength.

Figure 6:
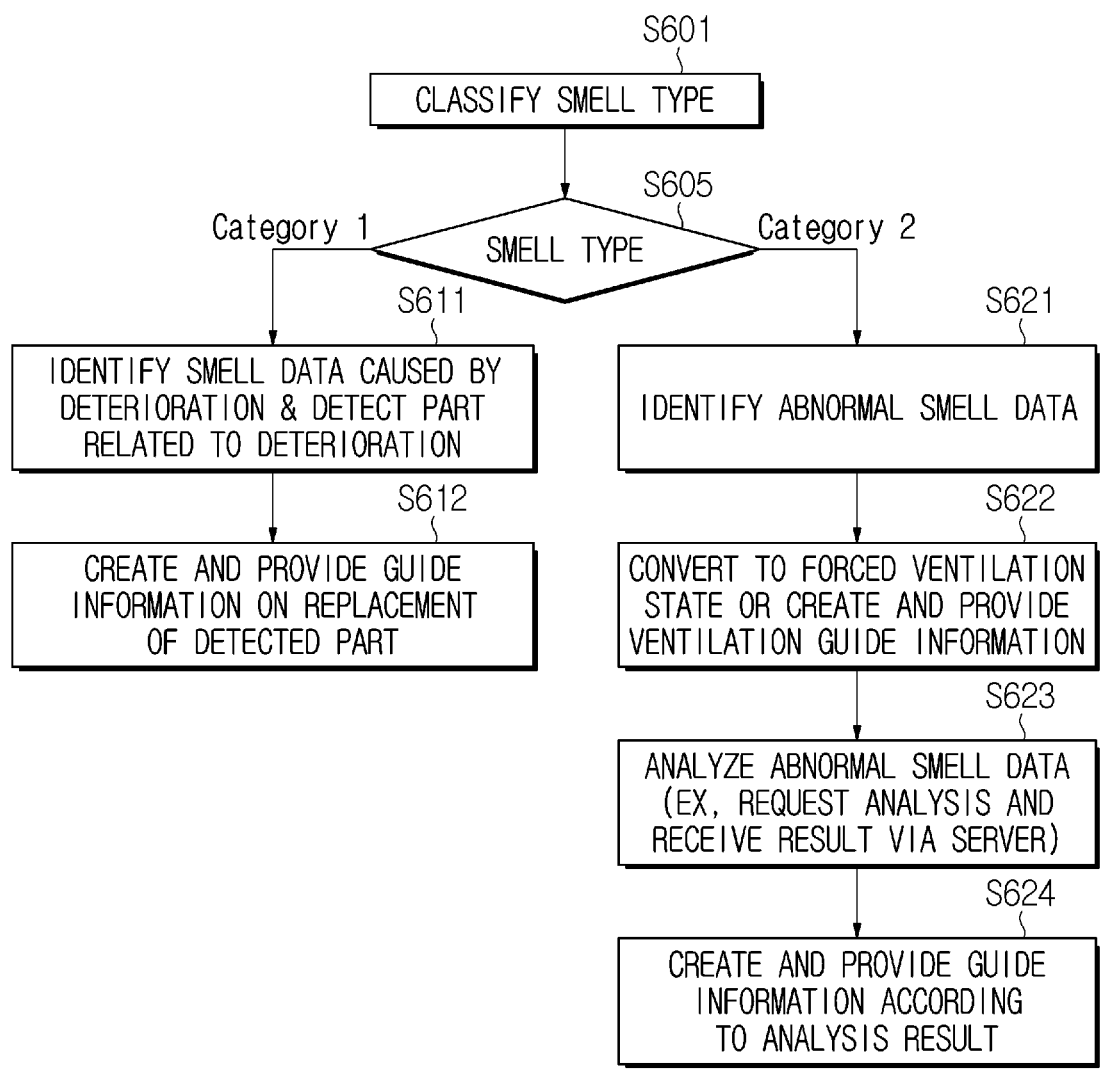
FIG. 6 is a flowchart illustrating a detailed operation of the step S500 of FIG. 5.
Figure 7A:
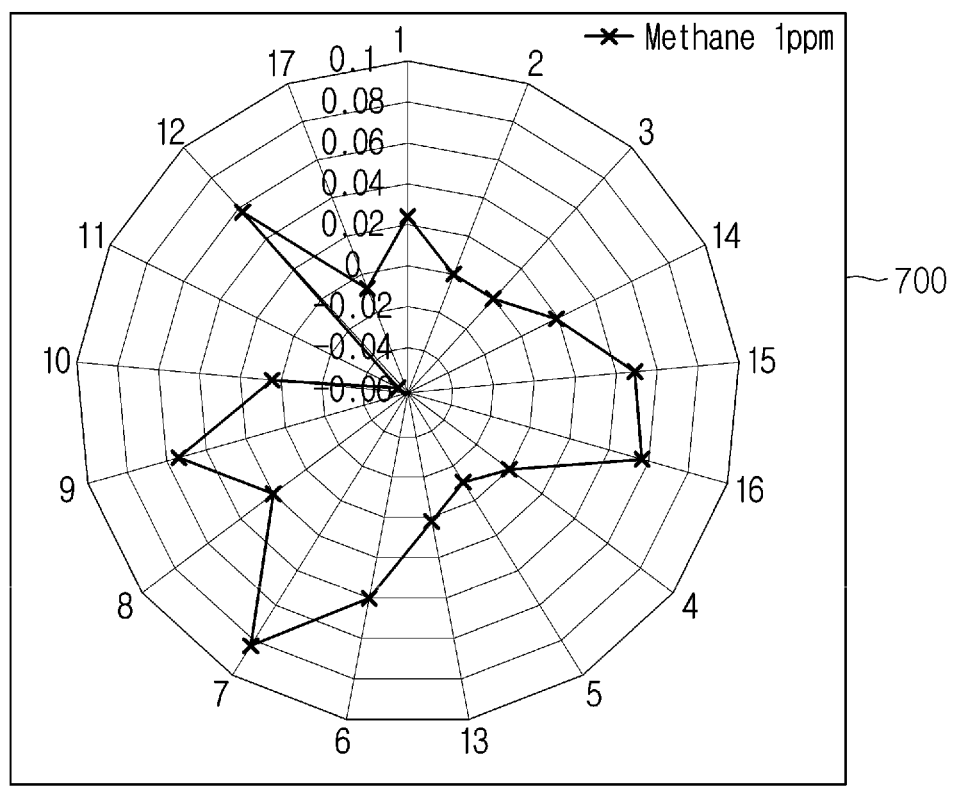
FIG. 7A and FIG. 7B are views illustrating gas component distribution patterns that are used in a method for providing a fleet service based on smell information according to an embodiment of the present disclosure.
Figure 7B:
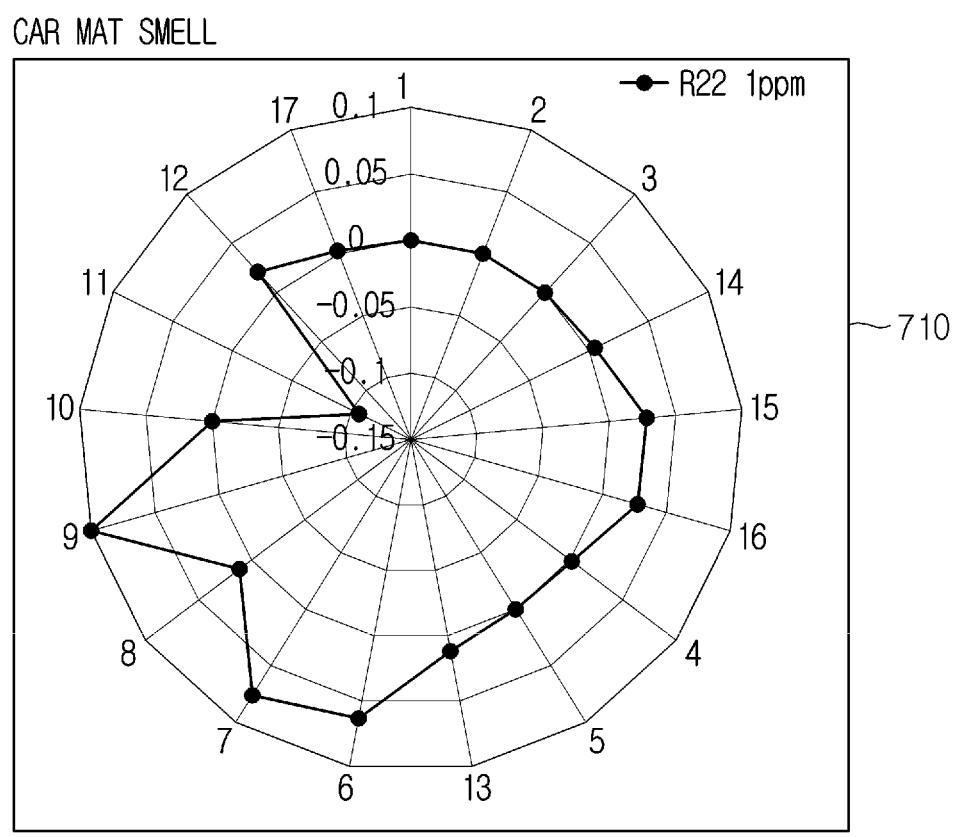

FIG. 6 is a flowchart illustrating a detailed operation of the step S500 of FIG. 5.

That is, FIG. 6 exemplifies in detail an operation of controlling driving of a moving object based on smell information that is detected in the moving object.

First, the moving object may identify smell information by using a smell analyzer. The smell information may include a smell type and smell strength at S601.

The smell analyzer may identify a smell type by using a multivariate analysis method at S605. For example, the smell analyzer may determine a smell type by analyzing a distribution pattern that displays multiple pieces of gas component data involving multiple variables. As an example, as exemplified in FIG. 7A and FIG. 7B, a distribution pattern displaying multiple pieces of gas component data may be identified. Distribution patterns 700 and 710 (refer to FIG. 7A and FIG. 7B) displayed by such multiple pieces of gas component data may be different according to each smell caused by an interior material or consumable provided in a moving object. Considering this, the smell analyzer may determine a smell type by comparing an identified distribution pattern and a distribution pattern that is set for each smell caused by an interior material or consumable.

As an example, a smell type may include a smell corresponding to an interior material or consumable provided in a moving object such as the smell of an air conditioner, a car mat smell, a car seat smell, a seat cover smell, a roof trim smell and the like. Such an interior material or consumable of a moving object undergoes a physical change or a chemical change according to cumulative usage time or cumulative usage distance, and the strength of a smell may change according to the degree of a physical change or a chemical change. In case the strength of a smell is relatively serious depending on the degree of a physical change or a chemical change, it is necessary to clean or replace an interior material or consumable provided in a moving object. Considering this, as it is necessary to identify which interior material or consumable causes a smell among interior materials or consumables in a moving object, a smell analyzer may detect in detail a smell of an air conditioner, a car mat smell, a car seat smell, a seat cover smell, a roof trim smell and the like.

In addition, since interior materials or consumables like an air conditioner, a car mat, a car seat, a seat cover and a roof trim have different characteristics, smells generated by each of those interior materials or consumables may cause different feelings of displeasure. Accordingly, different criteria for cleaning or replacing interior materials or consumables may be set by reflecting characteristics of interior materials or consumables like an air conditioner, a car mat, a car seat, a seat cover and a roof trim. For this, a smell analyzer may identify a smell strength according to each smell type.

Considering what is described above, the smell analyzer may identify a smell caused by an interior material or consumable and determine which interior material or consumable causes the smell at S611. Also, the smell analyzer may determine, based on a threshold corresponding to the determined interior material or consumable, whether the interior material or consumable needs to be cleaned or replaced and provide information thereon at S612.

Meanwhile, the smell analyzer may detect an abnormal smell different from the smell corresponding to an interior material or consumable at S621. In case the smell analyzer detects the abnormal smell, the moving object may identify the strength of the smell and control at least one ventilator in the moving object according to the strength of the smell thus identified at S622. Herein, the ventilator may include a window, a sunroof, an air inlet controller and the like in the moving object.

Furthermore, the moving object may control at least one ventilator by degrees according to the strength of the smell. As an example, in case the strength of the abnormal smell is level 1, the moving object may control an operation of the air inlet controller to make the outside air flow into the moving object. In addition, in case the strength of the abnormal smell is level 2, which is relatively higher than level 1, the moving object may control the operation of windows or sunroof system to make the outside air flow into the moving object.

As another example, the moving object may provide the strength of the abnormal smell to the user through a display unit or speaker installed in the moving object and also induce the user to control at least one ventilator.

Additionally, in case the strength of the smell is not lowered to a predetermined threshold even when the outside air flows in, the moving object may analyze the abnormal smell in detail at S623. The detailed analysis of the abnormal smell may be performed by means of an application installed in the moving object.

It is desirable that the detailed analysis of the abnormal smell is performed through the fleet service management server. As an example, after the moving object may deliver data, which are detected by the small analyzer, to the fleet service management server and request the fleet service management server to analyze the abnormal smell in detail, the fleet service management server may perform a detailed analysis of the abnormal smell and provide a result to the moving object. Next, the moving object may provide the result of the detailed analysis for the abnormal smell to the user through a display unit or speaker installed in the moving object and also induce the user to control at least one ventilator.

Furthermore, in case the result of the detailed analysis of the abnormal smell demands urgent cleaning of the moving object or replacement of an item in the moving object, the moving object may induce a move to a cleaning zone or an emergency maintenance zone at S624. As an example, the moving object may provide the result of the detailed analysis for the abnormal smell to the user through a display unit or speaker installed in the moving object. As another example, the moving object may retrieve a control right and control a move to a nearby cleaning zone or a nearby emergency maintenance zone.

Furthermore, a method for producing a result of the detailed analysis of the abnormal smell will be described in detail with reference to FIGS. 8 to 10.

Figure 8:
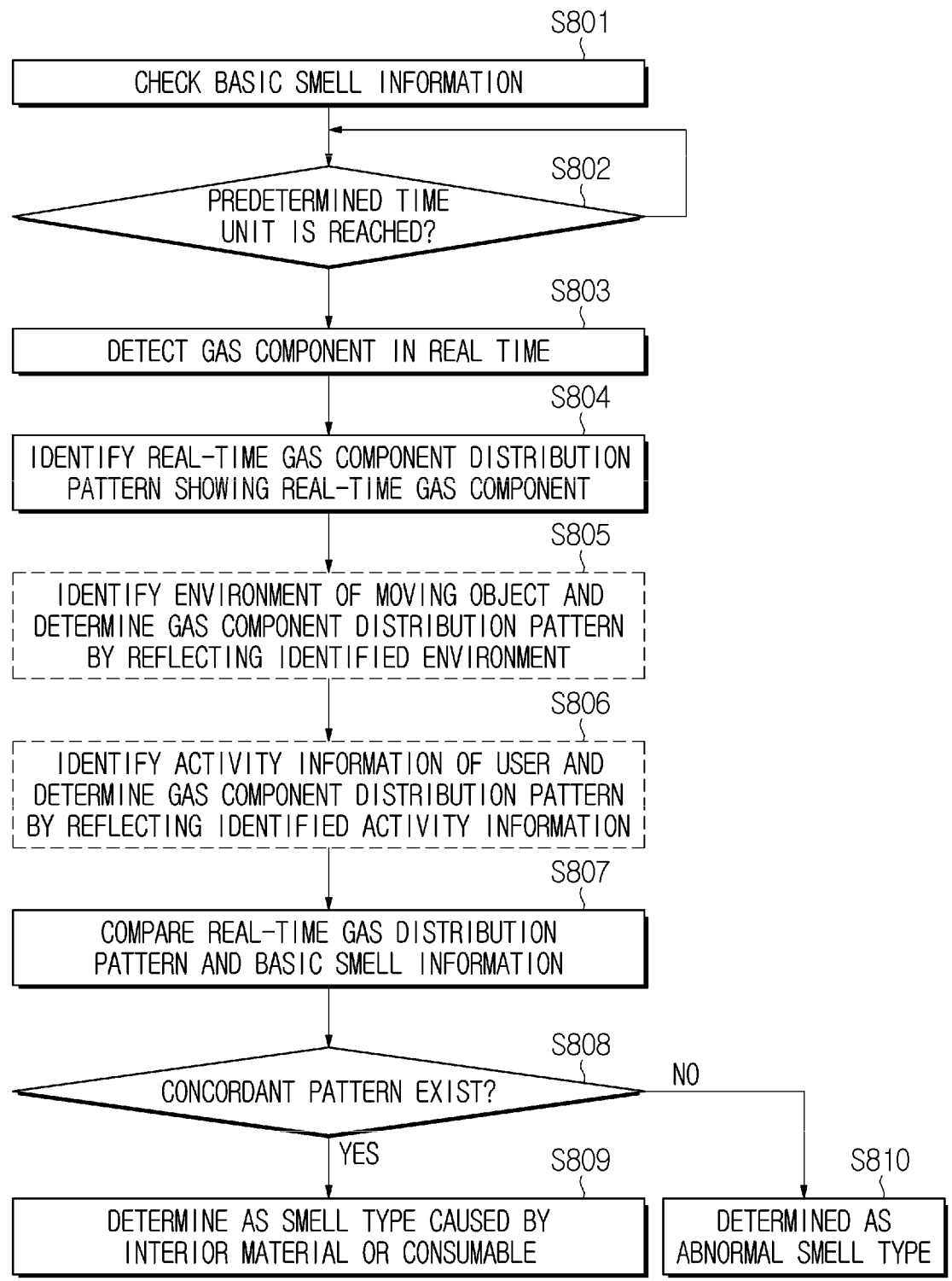
FIG. 8 is a view illustrating an operation of detecting a smell type in a method for providing a fleet service based on smell information according to an embodiment of the present disclosure.

FIG. 8 is a view illustrating an operation of detecting a smell type in a method for providing a fleet service based on smell information according to an embodiment of the present disclosure.

Referring to FIG. 8, an operation is exemplified in which a smell analyzer identifies a smell type.

First, a characteristic of a moving object, internal and external environments of the moving object, and the usage time of the moving object may be different, and smell information detected from such environments may vary according to a situation of the moving object. Considering this, the smell analyzer may detect smell information while a user is not using a moving object at S801. Thus, smell information, which is detected when a user is not using a moving object, is referred to as basic smell information, and a smell type and smell strength included in the basic smell information may be referred to as a basic smell type and basic smell strength respectively.

Basic smell information may be determined based on data that are measured while a user is not using a moving object and the outside air is shut off for a predetermined time. As an example, the smell analyzer may identify basic smell information based on data that are measured in a predetermined time (e.g., 2 hours) of shutting every car window and outside air after a user returns a moving object at S802. As an example, the smell analyzer may identify a gas component distribution pattern showing multiple pieces of gas component data. As a gas component distribution pattern showing such multiple pieces of gas component data may appear to be different according to smells caused by an interior material or consumable in a moving object, the smell analyzer may identify basic smell information caused by an interior material or consumable in the moving object by comparing an identified gas component distribution pattern and a gas component distribution pattern set to each smell caused by the interior material or consumable.

Furthermore, the smell analyzer may configure basic smell information by reflecting usage time of the moving object, operation distance of the moving object, a period of using an interior material or consumable of the moving object and the like all together.

Next, the smell analyzer may identify smell information on a predetermined time basis while the user is using the moving object at S803. In addition, the smell analyzer may compare current smell information thus detected and the basic smell information and check whether or not the two pieces of information agree with each other at S804. As an example, the smell analyzer may configure a basic air conditioner smell pattern by considering a gas component distribution pattern of a smell caused by an air conditioner of the moving object. In addition, the smell analyzer may configure a gas component distribution pattern, while the user is using the moving object at S807, and determine a smell type by checking whether or not the configured gas component distribution pattern agrees with the basic air conditioner smell pattern at S808.

In the same method as described above, the smell analyzer may configure and store basic smell patterns (e.g., car mat smell pattern, car seat smell pattern, roof trim smell pattern, etc.) for respective interior materials or consumables and determine a smell type by comparing a basic smell pattern and a gas component distribution pattern that is detected in real time at S809. If no condordant pattern exists, the smell analyzer determines the smell type as an abnormal smell type (S810).

Furthermore, the smell analyzer may reflect an environment of the moving object at a point of identifying a gas component distribution pattern at S805. As an example, the smell analyzer may determine a gas component distribution pattern by considering a window condition of the moving object, a setting of outside air inlet, the number of passengers, and the positions of the passengers. Specifically, the smell analyzer may identify a gas component property, which is displayed by such environmental characteristics as a window condition, a setting of outside air inlet, the number of passengers and the positions of the passengers, and process filtering of a gas component that is caused by the environmental characteristics. In addition, the smell analyzer may check a gas component distribution pattern under a condition in which the gas component is filtered.

Furthermore, in case the user visits a restaurant, a gas component may be detected which is caused by a food smell permeating the clothing of the user. As another example, in case the user visits a mart, a gas component may be detected which is caused by a product purchased by the user. Thus, according to an activity before the user gets on the moving object, smell strength or smell type may be detected differently. Considering this, the analyzer may reflect the user's activity information in detecting small strength or smell type at S806. As an example, the smell analyzer may identify information on a destination which the user has visited and detect smell strength or smell type by considering the information on the destination. Specifically, the smell analyzer may identify a gas component, which is attributable to the information on the destination, perform filtering of the identified gas component and then identify a gas component distribution pattern.

Furthermore, the user's activity information described above may be obtained by means of a device carried by the user. As an example, the device may drive an application related to using the moving object and identify location information of the moving object and payment information of the moving object while the application is being driven.

In addition, the device may estimate activity information by analyzing location information of the moving object and payment information of the moving object. As another example, the user's activity information may be also be obtained based on a route of the moving object. As an example, the moving object may identify information on a destination or waypoint of the moving object, which the user inputs through a navigation system, and also identify the user's activity information based on the information on the destination or waypoint.

Although, in an embodiment of the present disclosure, a method for estimating a user's activity information is exemplified, but the present disclosure is not limited thereto, and the method for estimating a user's activity information may be modified in various ways by those skilled in the art.

Figure 9:
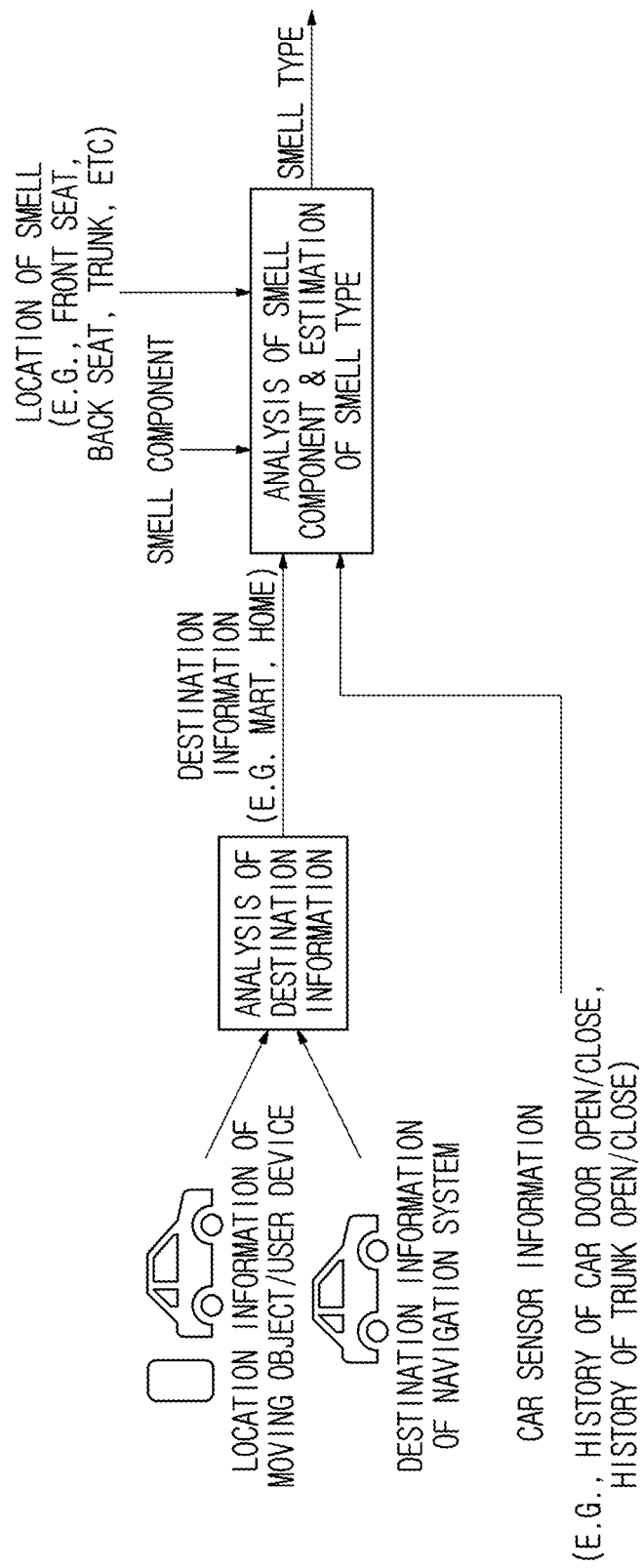
FIG. 9 is a view illustrating an operation of detecting a smell type in a method for providing a fleet service based on smell information according to an embodiment of the present disclosure.

FIG. 9 is a view illustrating an operation of detecting a smell type in a method for providing a fleet service based on smell information according to an embodiment of the present disclosure.

FIG. 9 exemplified in detail an operation of detecting a type of an abnormal smell.

As described above, a smell type may be determined based on a gas component, and such a gas component may be various depending on a situation. Accordingly, FIG. 9 presents a more effective way of detecting a type of an abnormal smell in a method for providing a fleet service based on smell information according to an embodiment of the present disclosure.

When a smell is determined to be an abnormal smell type, the smell analyzer needs to identify which matter or material causes the abnormal smell type. Accordingly, the smell analyzer may detect a main gas component showing a highest component value among multiple gas components that are detected. In addition, the smell analyzer may identify a matter or material related to such a main gas component and also identify a detailed smell type by comparing a gas component distribution pattern, which is shown by the matter or material, a gas component pattern that is currently detected.

Figure 10:
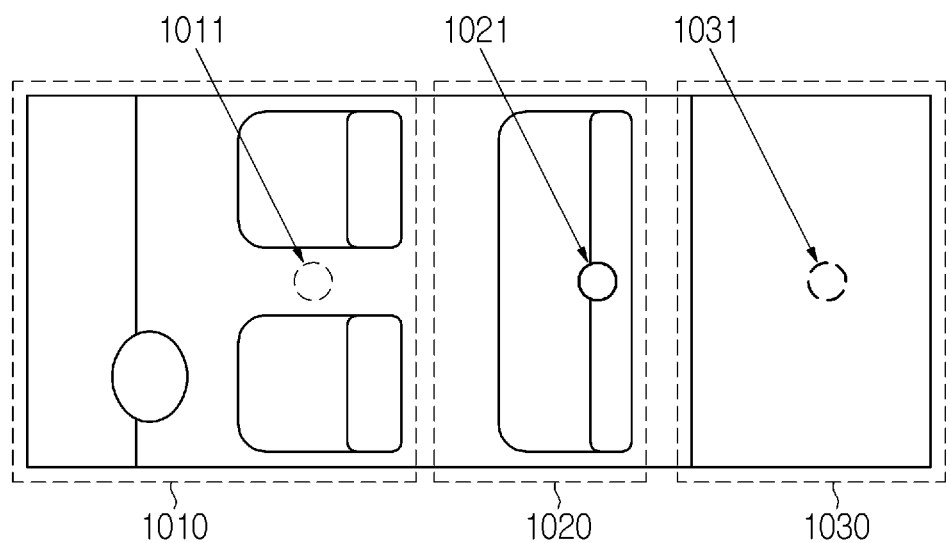
FIG. 10 is a view illustrating a multiplicity of smell sensors installed in a moving object according to an embodiment of the present disclosure.

Furthermore, referring to FIG. 10, the moving object may be equipped with a plurality of smell sensors 1011, 1021 and 1031. As an example, the plurality of smell sensors 1011, 1021 and 1031 may be prepared in a driver seat/passenger seat area 1010, in a backseat area 1020, and in a glove box(trunk) area 1030 in the moving object, and gas component data detected through the plurality of sensors 1011, 1021 and 1031 may be provided to the smell analyzer. Based on this, the smell analyzer may detect an area showing a relatively high level of a gas component, that is, a main gas component, which is detected in the driver seat/passenger seat area 1010, in the backseat area 1020 and in the glove box (trunk) area 1030, and thus estimate an area causing a smell. The smell analyzer may identify a detailed smell type by further reflecting such a smell-causing area. As an example, in case the smell-causing area is the driver seat/passenger seat area 1010 or the backseat area 1020, the smell analyzer may extract first a matter or material that may be loaded or got in the driver seat/passenger seat area 1010 or the backseat area 1020. In addition, the smell analyzer may identify the detailed smell type by comparing a gas component distribution pattern, which is displayed by the extracted matter or material, and a gas component pattern that is currently detected. Likewise, in case the smell-causing area is the glove box (trunk) 1030, the smell analyzer may extract first a matter or material that may be loaded or got in the glove box (trunk) area 1030 of the moving object. In addition, the smell analyzer may identify the detailed smell type by comparing a gas component distribution pattern, which is displayed by the extracted matter or material, and a gas component pattern that is currently detected.

Furthermore, in case the user visits a mart, a gas component may be detected which is caused by a product purchased by the user. Thus, according to an activity before the user gets on the moving object, smell strength or smell type may be detected differently. Considering this, the analyzer may reflect the user's activity information in detecting small strength or smell type. As an example, the smell analyzer may identify information on a destination which the user has visited and detect smell strength or smell type by considering the information on the destination. Specifically, the smell analyzer may identify a gas component, which is attributable to the information on the destination, perform filtering of the identified gas component and then identify a gas component distribution pattern.

Furthermore, the user's activity information described above may be obtained by means of a device carried by the user. As an example, the device may drive an application related to using the moving object and identify location information of the moving object and payment information of the moving object while the application is being driven. In addition, the device may estimate activity information by analyzing location information of the moving object and payment information of the moving object. As another example, the user's activity information may be also be obtained based on a route of the moving object. As an example, the moving object may identify information on a destination or waypoint of the moving object, which the user inputs through a navigation system, and also identify the user's activity information based on the information on the destination or waypoint.

Although, in an embodiment of the present disclosure, a method for estimating a user's activity information is exemplified, but the present disclosure is not limited thereto, and the method for estimating a user's activity information may be modified in various ways by those skilled in the art.

Figure 11:
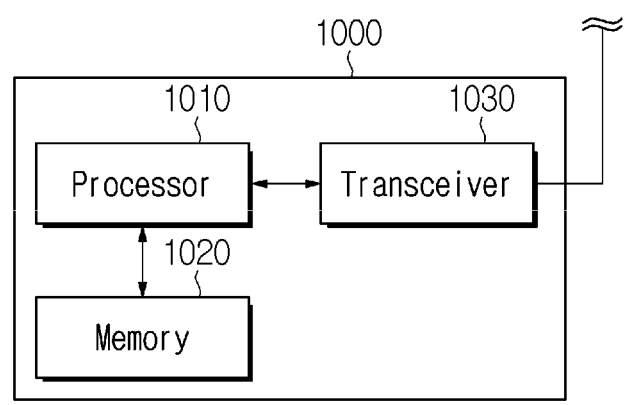
FIG. 11 is a view illustrating an apparatus configuration according to an embodiment of the present disclosure.

FIG. 11 is a view illustrating an apparatus configuration according to an embodiment of the present disclosure.

Referring to FIG. 11, the apparatus may include at least one of the above-described moving object, a device, a server and an RSU. In other words, the apparatus may be configured to communicate and work with another device. The present disclosure is not limited to the above-described embodiment. For example, for the above-described operation, an apparatus 1000 may include one or more among a processor 1010, a memory 1020, and a transceiver 1030. In other words, the apparatus may include a necessary configuration for communicating with another apparatus. In addition, the apparatus may include another configuration apart from the above-described configuration. In other words, the apparatus may have a configuration, which includes the above-described apparatus for communicating with another device but is not limited thereto, and may be operated based on what is described above.

Although the exemplary methods of the present disclosure described above are represented by a series of acts for clarity of explanation, they are not intended to limit the order in which the steps are performed, and if necessary, each step may be performed simultaneously or in a different order. In order to implement a method according to the present disclosure, the illustrative steps may include an additional step or exclude some steps while including the remaining steps. Alternatively, some steps may be excluded while additional steps are included.

The various exemplary embodiments of the disclosure are not intended to be all-inclusive and are intended to illustrate representative aspects of the disclosure, and the features described in the various exemplary embodiments may be applied independently or in a combination of two or more. In addition, the various exemplary embodiments of the present disclosure may be implemented by hardware, firmware, software, or a combination thereof. In the case of hardware implementation, one or more application specific integrated circuits (ASICs), digital signal processors (DSPs), digital signal processing devices (DSPDs), programmable logic devices (PLDs), field programmable gate arrays. A general processor, a controller, a microcontroller, a microprocessor, and the like may be used for implementation.

The scope of the present disclosure includes software or machine-executable instructions (for example, an operating system, applications, firmware, programs, etc.) that enable operations according to the methods of various exemplary embodiments to be performed on a device or computer, and a non-transitory computer-readable medium in which such software or instructions are stored and are executable on a device or computer.

While a number of exemplary aspects and embodiments have been discussed above, those of skill in the art will recognize that still further modifications, permutations, additions and sub-combinations thereof of the features of the disclosed embodiments are still possible. It is therefore intended that the following appended claims and claims hereafter introduced are interpreted to include all such modifications, permutations, additions and sub-combinations as are within their true spirit and scope.

The invention claimed is:

1. A method for providing a fleet service based on smell information, the method comprising:
    monitoring, by a monitoring unit, smell information of a moving object that is used in a fleet system;
    controlling, by a processor, an operation of the moving object based on the smell information; and
    determining a return zone of the moving object based on the smell information;
    wherein the monitoring of the smell information of the moving object comprises checking at least one of a smell type and a smell strength;
    wherein the smell type comprises at least one of an abnormal smell, a smell caused by an interior material, a smell caused by a consumable of the moving object, and a combination thereof; and
    wherein the checking of at least one of the smell type and the smell strength comprises checking a basic smell pattern based on data that are measured while the user does not use the moving object and the outside air is shut off for a predetermined time.

2. The method of claim 1, wherein the controlling of the operation of the moving object comprises controlling to make outside air flow into the moving object in response to the smell strength that comes to exceed a predetermined threshold.

3. The method of claim 1, wherein the controlling of the operation of the moving object comprises providing at least one of the smell type and the smell strength through an entity capable of being recognized by the user.

4. The method of claim 1, wherein the monitoring of the smell information of the moving object comprises checking the smell strength according to the smell type.

5. The method of claim 1, wherein the determining of the return zone of the moving object comprises determining the return zone of the moving object as a cleaning zone when the smell strength exceeds a predetermined first threshold.

6. The method of claim 5, wherein the determining of the return zone of the moving object comprises determining the return zone of the moving object as an emergency maintenance zone when the smell strength exceeds a predetermined second threshold.

7. The method of claim 5, wherein the smell strength comprises a smell strength corresponding to each of the smell types.

8. The method of claim 5, wherein the smell strength comprises a strength for the abnormal smell.

9. The method of claim 1, wherein the checking of at least one of the smell type and the smell strength comprises:
    checking a current gas component distribution pattern based on data, which are measured while the user uses the moving object; and
    determining the smell type by using a result of comparison between the basic smell pattern and the current gas component distribution pattern.

10. The method of claim 9, wherein the checking of at least one of the smell type and the smell strength comprises:
    checking environment information of the moving object; and
    determining the smell type by considering the environment information of the moving object and the current gas component distribution pattern.

11. The method of claim 9, wherein the checking of at least one of the smell type and the smell strength comprises:
    checking activity information of the user; and
    determining the smell type by considering the activity information of the user and the current gas component distribution pattern.

12. The method of claim 1, wherein the monitoring of the smell information of the moving object comprises:
    detecting smell information that is generated from at least one zone of the moving object; and
    monitoring the smell information of the moving object by using at least one piece of smell information corresponding to the at least one zone.

13. A moving object for a fleet service, the moving object comprising:
    at least one transceiver;
    at least one smell sensor;
    a smell information monitoring unit, which is configured to monitor smell information based on data detected from the smell sensor; and
    at least one processor configured to control the at least one transceiver and the smell information monitoring unit;
    wherein the at least one processor is configured to:
    control an operation of the moving object based on the smell information;
    identify a return zone of the moving object based on the smell information; and
    provide the return zone of the moving object;
    wherein the smell information monitoring unit is further configured to check at least one of a smell type and a smell strength;
    wherein the smell type comprises at least one of an abnormal smell, a smell caused by an interior material, a smell caused by a consumable of the moving object, and a combination thereof; and
    wherein the checking of at least one of the smell type and the smell strength comprises checking a basic smell pattern based on data that are measured while the user does not use the moving object and the outside air is shut off for a predetermined time.

14. A server apparatus for managing a fleet service, the apparatus comprising:
- at least one transceiver configured to transmit and receive a signal; and
- at least one processor configured to control the at least one transceiver, to provide the fleet service through at least one moving object or at least one user terminal, to identify smell information provided from the at least one moving object, to identify a return zone of the moving object based on the smell information, and to manage the return zone of the moving object;
- wherein the smell information is provided by checking at least one of a smell type and a smell strength;
- wherein the smell type comprises at least one of an abnormal smell, a smell caused by an interior material, a smell caused by a consumable of the moving object, and a combination thereof; and
- wherein the checking of at least one of the smell type and the smell strength comprises checking a basic smell pattern based on data that are measured while the user does not use the moving object and the outside air is shut off for a predetermined time.

15. The apparatus of claim 14, wherein the at least one processor is configured to determine the return zone of the moving object based on the smell information.

16. The apparatus of claim 14, wherein the at least one processor is configured to determine a basic smell pattern based on data that are measured while the user does not use the moving object and the outside air is shut off for a predetermined time.

17. The apparatus of claim 16, wherein the at least one processor is configured to:
- determine a current gas component distribution pattern based on data measured while the user uses the moving object; and
- determine the smell type by using a result of comparison between the basic smell pattern and the current gas component distribution pattern.

* * * * *